US005589571A

United States Patent [19]

King

[11] Patent Number: 5,589,571
[45] Date of Patent: *Dec. 31, 1996

[54] PROCESS FOR PRODUCTION OF INHIBITED FORMS OF ACTIVATED BLOOD FACTORS

[75] Inventor: Robert King, Fremont, Calif.

[73] Assignee: COR Therapeutics, Inc., South San Francisco, Calif.

[*] Notice: The term of this patent shall not extend beyond the expiration date of Pat. No. 5,589,572.

[21] Appl. No.: 330,978

[22] Filed: Oct. 28, 1994

[51] Int. Cl.$^6$ ............ C07K 14/745; C07K 1/18; A61K 38/36; C12P 21/06
[52] U.S. Cl. ............ 530/381; 435/68.1; 530/384; 530/413; 530/829
[58] Field of Search ............ 530/381, 382, 530/383, 384, 412, 413, 829, 830; 435/68.1; 514/12, 21

[56] References Cited

U.S. PATENT DOCUMENTS

| | | | |
|---|---|---|---|
| 4,285,932 | 8/1981 | Smith | 424/94.64 |
| 4,318,904 | 3/1982 | Shaw et al. | 514/18 |
| 4,337,244 | 6/1982 | Smith | 424/94.64 |
| 4,447,416 | 5/1984 | Menache-Aronson | 514/2 |
| 4,604,285 | 8/1986 | Smith et al. | 424/94.6 |
| 4,721,572 | 1/1988 | Jordan | 210/635 |
| 4,725,673 | 2/1988 | Herring | 530/381 |
| 5,071,961 | 12/1991 | Kraus et al. | 530/384 |
| 5,120,537 | 6/1992 | Esmon et al. | 424/94.64 |
| 5,153,166 | 10/1992 | Jain et al. | 502/402 |
| 5,153,175 | 10/1992 | Krueger et al. | 514/12 |
| 5,278,144 | 1/1994 | Wolf | 514/12 |
| 5,279,956 | 1/1994 | Griffin et al. | 435/183 |

FOREIGN PATENT DOCUMENTS

| 0286323 | 3/1988 | European Pat. Off. . |
|---|---|---|
| WO89/05650 | 12/1988 | WIPO . |

OTHER PUBLICATIONS

Ahmad, et al., "Rapid Purification of Factor IX, Factor X and Prothrombin by Immunoaffinity and Ion Exchange Chromatography," *Thrombosis Research* (1989) 55:121–133.

Aronson, et al., "Two Forms of the Human Prothrombin Converting Enzyme (Active Factor X) (35769)," *Two Forms of X*, (1971) 137:4, 1262–1266.

Bajaj, et al., "A Simplified Procedure for Purification of Human Prothrombin, Factor IX and Factor X," *Preparative Biochemistry* (1981) 11:4, 397–412.

Bauer, et al., "Detection of Factor X Activation in Humans," *Blood* (1989) 74:6 (Nov. 1), 2007–2015.

Benedict, et al. "Active Site–Blocked Factor Xa Prevents Thrombus Formation in the Coronary Vasculature in Parallel With Inhibition of Extravascular Coagulation in a Canine Thrombosis Model," *Blood* (1993) 81:8, 2059–2066.

Cassels, et al. "The Interaction of Streptokinase Plasminogen Activator Complex Tissue–Type Plasminogen Activator, Urokinase and their Acylated Derivatives with Fibrin and Cyanogen Bromide Digest of Fibrinogen," *Biochem. J.* (1987) vol. 247, 395–400.

Chattopadhyay, et al. "Molecular Recognition in the Activation of Human Blood Coagulation Factor X," *The Journal of Biological Chemistry,* (1989) 264:19, 11035–11043.

Claeson, "Synthetic Peptides and Peptidomimetics as Substrates and Inhibitors of Thrombin and Other Proteases in the Blood Coagulation System," *Blood Coagulation and Fibrinolysis* (1994) 5, 411–436.

Colman, et al. "Section A, Plasma Coagulation Factors," *Plasma Coagulation Factors*, 3–17.

Crabbe, et al. "Acylated Plasminogen–Streptokinase Activator Complex: A New Approach to Thrombolytic Therapy," *Pharmacotherapy* (1990) 10:2, 115–126.

Davie, "Chapter 16, The Blood Coagulation Factors: Their cDNAs, Genes, and Expression," *Plasma Coagulation Factors*, Part 1, Section A, 242–268.

Di Scipio, et al., "Activation of Human Factor X (Stuart Factor) by a Protease from Russell's Viper Venom, Activation of Human Factor X," *Biochemistry* (1977) 16:24, 5253–5260.

Etingin, et al., "Viral Activation of the Coagulation Cascade: Molecular Interactions at the Surface of Infected Endothelial Cells," *Cell* (1990) 61:657–662.

Fears, "Development of Anisoylated Plasminogen–Streptokinase Activator Complex from the Acyl Enzyme Concept," *Seminars in Thrombosis and Hemostasis* (1980) 15:2, 129–139.

Fears, et al., "The Protective Effect of Acylation on the Stability of Anisoylated Plasminogen Streptokinase Activator Complex in Human Plasma," *Drugs* (1987) 33 (Suppl. 3), 57–63.

Friedberg, et al., "Large Scale Purification of Factor X by Hydrophobic Chromatography," *Preparative Biochemistry* (1988) 18:3, 303–320.

Furie, et al., "Coagulant Protein of Russell's Viper Venom," *Blood Clotting Enzymes*, Methods in Enzymology, (1976) 45, 191–205.

Furie, et al., "The Molecular Basis of Blood Coagulation," *Cell* (1988) 53:505–518.

Gordon, et al., "The Site of Activation of Factor X by Cancer Procoagulant," *Blood Coagulation and Fibrinolyses* (1991) 2:735–739.

Hoover, et al., "The Adhesive Interaction between Polymorphonuclear Leukocytes and Endothelial Cells in Vitro," *Cell* (1978) 14: 423–428.

(List continued on next page.)

Primary Examiner—Mindy Fleisher
Assistant Examiner—Nancy J. Degen
Attorney, Agent, or Firm—Morrison & Foerster LLP

[57] ABSTRACT

A process for producing a highly purified preparation of an inhibited form of an activated blood factor entails providing a partially purified preparation containing the blood factor of interest, treating the partially purified preparation to convert the blood factor to an inhibited activated form in a single step, and then purifying the resulting inhibited activated blood factor.

16 Claims, 4 Drawing Sheets

OTHER PUBLICATIONS

Hrinda, et al., "Preclinical Studies of a Monoclonal Antibody–Purified Factor IX, Mononine™," *Seminars in Hematology* (1991) 28:3, Suppl. 6 (Jul.), 6–14.

Jesty, "Analysis of the Generation and Inhibition of Activated Coagulation Factor X in Pure Systems and in Human Plasma," *The Journal of Biological Chemistry* (1986) 261:19, 8695–8702.

Kettner, et al., "Synthesis of Peptides of Arginine Chloromethyl Ketone. Selective Inactivation of Human Plasma Kallikrein," *Biochemistry*, (1978) 17:22, 4778–4783.

Kettner, et al., "The Susceptibility of Urokinase to Affinity Labeling by Peptides of Arginine Chloromethyl Ketone," *Biochimica et Biophysica Acta* (1979) 569:31–40.

Kettner, et al., "Active Site Mapping of Human and Rat Urinary Kallikreins by Peptidyl Chloromethyl Ketones," *Archives of Biochemistry and Biophysics* (1980) 202:2, 420–430.

Kettner, et al., "Inactivation of Trypsin–Like Enzymes with Peptides of Arginine Chloromethyl Ketone," *Methods in Enzymology* (1981) 80:826–842.

Kettner, et al., "The Selective Affinity Labeling of Factor $X_a$ by Peptides of Arginine Chloromethyl Ketone," *Thrombosis Research* (1981) 22:645–652.

Kosow, "Purification and Activation of Human Factor X: Cooperative Effect of $Ca^{++}$ on the Activation Reaction," *Thrombosis Research* (1976) 9:565–573.

Lijnen, et al., "Inhibition of Tryspin–Like Serine Proteinases by Tripeptide Arginyl and Lysyl Chloromethylketones," *Thrombosis Research* (1984) 34:431–437.

Marsh, "Snake Venoms Affecting the Haemostatic Mechanism—a Consideration of their Mechanisms, Practical Applications and Biological Significance," *Blood Coagulation and Fibrinolysis* (1994) 5:399–410.

Mertens, et al., "Pathways in the Activation of Human Coagulation Factor X," *Biochem. J.* (1980) 185:647–658.

Miletich, et al., "The Synthesis of Sulfated Dextran Beads for Isolation of Human Plasma Coagulation Factors II, IX and X," *Analytical Biochemistry*, (1980) 105:304–310.

Monahan, et al., "Identification of Human Cohn Fraction III as a Useful Source for the Simultaneous Purification of FIX and FX Zymogens," *Thrombosis Research* (1980) 19:743–755.

Nesheim, et al., "The Contribution of Bovine Factor V and Factor Va to the Activity of Prothrombinase," *The Journal of Biological Chemistry* (1979) 254:21, 10952–10962.

Nesheim, et al., "Cofactor Dependence of Factor Xa Incorporation into the Prothrombinase Complex," *The Journal of Biological Chemistry* (1981) 256:13, 6537–6540.

Sinha, et al., "Procoagulation Activities of Reversibly Acylated Forms of Factor Xa," *Blood*, (1995) 86:4153–4157.

Steinberg, et al., "Activation of Factor X", *Plasma Coagulation Factors*, Part 1, Section A, Chapter 7, 112–119.

Sturzebecker, J., et al., "Acyl–Derivatives of tPA," *Thrombosis Research* (1987) 47:6, 699–703 (first page missing).

Williams, et al., "Zymogen/Enzyme Discrimination Using Peptide Chloromethyl Ketones," *The Journal of Biological Chemistry* (1989) 264:13, 7536–7545.

PROCESS FOR PRODUCTION OF INHIBITED FORMS OF ACTIVATED BLOOD FACTORS

FIELD OF THE INVENTION

This invention relates to the production of blood factors, and particularly this invention relates to large-scale production of purified inhibited forms of activated blood factors.

BACKGROUND OF THE INVENTION

Following initiation of the clotting process, blood coagulation proceeds through the sequential activation of certain plasma proenzymes to their enzyme forms. These plasma glycoproteins, including Factor XII, Factor XI, Factor IX, Factor X, Factor VII, and prothrombin, are zymogens of serine proteases. Most of these blood clotting enzymes are effective on a physiological scale only when assembled in complexes on membrane surfaces with protein cofactors such as Factor VIII and Factor V. Other blood factors modulate and localize clot formation, or dissolve blood clots. Activated protein C is a specific enzyme that inactivates procoagulant components. Calcium ions are involved in many of the component reactions. Blood coagulation follows either the intrinsic pathway, where all of the protein components are present in blood, or the extrinsic pathway, where the cell-membrane protein tissue factor plays a critical role. Clot formation occurs when fibrinogen is cleaved by thrombin to form fibrin. Blood clots are composed of activated platelets and fibrin.

Thrombin is a multifunctional protease that regulates several key biological processes. For example thrombin is among the most potent of the known platelet activators. In addition, as noted above, thrombin is essential for the cleavage of fibrinogen to fibrin to initiate clot formation. These two elements are involved in normal hemostasis but in atherosclerotic arteries can initiate the formation of a thrombus, which is a major factor in pathogenesis of vasoocclusive conditions such as myocardial infarction, unstable angina, nonhemorrhagic stroke and reocclusion of coronary arteries after angioplasty or thrombolytic therapy. Thrombin is also a potent inducer of smooth cell proliferation and may therefore be involved in a variety of proliferative responses such as restenosis after angioplasty and graft induced atherosclerosis. In addition, thrombin is chemotactic for leukocytes and may therefore play a role in inflammation, Hoover, R. J. et al., *Cell* 14:423 (1978); Etingin, O. R. et al., *Cell* 61:657 (1990). These observations indicate that inhibition of thrombin formation or inhibition of thrombin itself may be effective in preventing or treating thrombosis, limiting restenosis and controlling inflammation.

The formation of thrombin is the result of the proteolytic cleavage of its precursor prothrombin at the Arg-Thr linkage at positions 271–272 and the Arg-Ile linkage at positions 320–321. This activation is catalyzed by the prothrombinase complex, which is assembled on the membrane surfaces of platelets, monocytes, and endothelial cells. The complex consists of Factor Xa (a serine protease), Factor Va (a cofactor), calcium ions and the acidic phospholipid surface. Factor Xa is the activated form of its precursor, Factor X, which is secreted by the liver as a 58 kDa precursor and is converted to the active form, Factor Xa, in both the extrinsic and intrinsic blood coagulation pathways. It is known that the circulating levels of Factor X, and of the precursor of Factor Va, Factor V, are on the order of $10\text{-}7_M$. There has been no determination of the levels of the corresponding active Factors Va and Xa.

The amino acid sequences and genes of most of the plasma proteins involved in hemostasis of blood are commonly known, such as Factor IIa, Factor Va, Factor VIIa, Factor IXa, Factor Xa, Factor XIa, Factor XIIa, Activated Protein C, Activated Protein S, fibrinogen and thrombin. Also commonly known are the amino acid sequences and genes of the precursor forms of these blood factors, and common methods for their activation or conversion to mature forms.

Factor X (Stuart Factor) is an essential component of the blood coagulation cascade (see, FIGS. 1 and 2). Factor X is a member of the calcium ion binding, gamma carboxyglutamyl ("Gla")-containing, vitamin K dependent, blood coagulation glycoprotein family, which also includes Factors VII and IX, prothrombin, protein C and protein S, Furie, B. et al., *Cell* 53:505 (1988). Factor X is the zymogen for the serine protease Factor Xa. Factor Xa combines with a co-factor, activated Factor V, calcium, and phospholipids on a membrane surface to form the prothrombinase complex. This enzyme complex converts prothrombin to thrombin, which then converts fibrinogen to fibrin, one of the pathways resulting in thrombosis (Colman, R. W. et al., "Overview of Hemostasis" in Colman, R. W., et al., *Hemostatis and Thrombosis, Basic Principles and Clinical Practice,* Second Edition (1987), Part I, Section A, Plasma Coagulation Factors, pp. 3–17).

Factor X can be purified from natural, synthetic or recombinant sources by any of a number of different extractive and chromatographic techniques, such as: a combination of ion-exchange, heparin-affinity and hydroxylapatite chromatography (Kosow, D. P., *Thromb. Res.,* 9(6):565–573 (1976); sulfated dextran (Miletich, J. P. et al., *Analytical Biochemistry* 105:304–310 (1980)); a combination of barium citrate adsorption, ammonium sulfate precipitation, ion-exchange and heparin-affinity chromatography (Bajaj, S. P. et al., *Prep. Biochem.* 11:397–412 (1981)); Cohn fractionation (Monohan, J. B. et al., *Thromb. Res.* 19(6):743–755 (1980)); sulfated non-carbohydrate matrices (U.S. Pat. No. 4,721,572; and U.S. Pat. No. 4,725,673); immunoaffinity chromatography (European Patent Application 0 286,323); hydrophobic interaction chromatography (Freidberg, R. C., et al., *Prep. Biochem.* 18(3):303–320 (1988)); metal-chelate chromatography (PCT/GB88/01150); a combination of immunoaffinity and ion-exchange (Ahmad, S. S. et al., *Thromb. Res.* 55(1):121–133 (1989)); and as a by-product in the purification of other blood coagulation factors (Hrinda, M. E., et al., "Preclinical Studies of a Monoclonal Antibody-Purified Factor IX, Mononine™," in *Seminars in Hematology* 28(3) Suppl. 6:6–14 (1991); and U.S. Pat. No. 5,071,961.) Typically, Factor X activation, inactivation and purification are accomplished separately.

Factor X must be activated to Factor Xa before the protease is incorporated into the prothrombinase complex (Steinberg, M. et al., "Activation of Factor X" in Colman, R. W. et al., supra, Part I, Section A, Chapter 7, pp 112–119). Factor Xa is a two chain molecule linked by one disulfide bond between the two chains. The heavy chain contains the serine protease, trypsin-like active site and the N-terminal activation peptide which is glycosylated. The heavy chain has at least three forms, a, β and g, which differ due to the cleavage of a C-terminal peptide in the heavy chain (Aronson, D. L. et al., *Proc. Soc. Exp. Biol. Med.* 137(4):1262–1266 (1971); Mertens, K. et al., *Biochem J.* 185:647–658 (1980)). This C-terminal peptide is thought to be glycosylated through an O-linked type glycosylation. The a form is the full length form of the heavy chain and the β and g forms are clipped. The light chain contains a growth factor-like domain and a number of unique post-translationally modified amino acid residues, called gamma-carboxy glutamic acid residues ("GLA's") which are implicated in imparting activity through calcium binding interactions required in the prothrombinase complex (Davie, E. W., "The Blood Coagulation Factors: Their cDNAS, Genes and Expression" in Colman, R. W. et al., supra, Part I, Section A, pp. 242–268).

Factor X can be activated to Factor Xa by any of several methods. Factor X is activated naturally through the extrinsic pathway (Factor VIIa/Tissue Factor complex) or the intrinsic pathway (Factor VIIIa/Factor Ixa-phospholipid-calcium enzyme complex) (Mertens, K. et al., *Biochem J.* 185:647–658 (1980); Jesty, J., *J. Biol. Chem.* 261(19):8695–8702 (1986); Steinberg, M. et al., supra; Bauer, K. et al., *Blood* 74(6):2007–2015 (1989); Chattopadhyay, A. et al., *J. Biol. Chem.* 2:735–739 (1989)). Factor X can also be activated to Factor Xa by proteases such as Russell's Viper Venom Factor X activating enzyme ("RVV-X") (Furie, B. C. et al., *Methods in Enzymology* 45:191–205 (1976); DiScipio, R. G. et al., *Biochemistry* 16(24):5253–5260 (1977); trypsin (Steinberg, M., et al., supra); or cancer procoagulant (Gordon, S. G. et al., *Blood Coagulation and Fibrinolysis* 2:735–739 (1991)).

It is known that numerous snake venom activities affect the intrinsic coagulation mechanism by variously activating, inhibiting or converting factors in the blood coagulation cascade; snake venoms are known which activate Protein C, prothrombin, thrombin-like enzymes, fibrinogenases, and activities of Factors V and X (N. A. Marsh, *Blood Coagulation and Fibrinolysis* 5:399–410 (1994). Synthetic peptides and peptidomimetics are also known as substrates and inhibitors of serine proteases (Claeson, G., *Blood Coagulation and Fibrinolysis* 5:411–436 (1994). A number of general and specific serine protease inhibitors are also known.

Various activators and inhibitors are commonly known for many of the blood factors. For example, Factor I (fibrinogen) is known to be activated by thrombin; Factor II (prothrombin) is known to be activated by Factor Xa and thrombin; Factor V is known to be activated by papain, a Factor-V-activation protease from Russell viper venom, plasmin, Factor Xa, chymotrypsin, and thrombocytin, and is inactivated by activated Protein C; Factor VII is known to be activated by minor proteolysis, with a signal peptidase and a processing protease; Factor IX is known to be activated by Factor XIa with calcium ions, tissue factor, Factor VII, and Russell viper venom-X, and is known to be inactivated by hirudin and antithrombin III; Factor X is activated by Factors IXa and VII with phospholipid and calcium ions, and by Russell viper venom; Factor XI is known to be activated by Factor XIIa and trypsin; Factor XII is known to be activated by contact with negatively charged surfaces, sulfatides, trypsin, plasmin, and kallikrein; Protein C is activated by thrombin, etc. See, Colman et al., supra. for the text describing known blood factor activators and inactivators.

In some circumstances, it is desirable to interfere with the functioning of Factor Xa in order to prevent excessive clotting. In other circumstances, such as in hemophilia, it is desirable to provide a source of Factor Xa independent of the activation process that takes place in normal individuals. Both of the common forms of hemophilia (hemophilia A and B) involve deficiencies in only the intrinsic pathway of activation, but the operation of the extrinsic pathway does not appear to be successful in arresting bleeding. Similarly, other patients are treated currently for deficiencies of other blood factors (such as VII, X, XI, XIII), or von Willebrand's disease. Factor VII deficiency is not as clinically well-defined as hemophilia A or B, however patients with Factor VII deficiency have been reported to have extensive bleeding. Protein C deficiency is associated with thrombotic risk.

Factor Xa, and several other activated blood factors, have typically not been useful as pharmaceuticals because of their extremely short half-life in serum, which for example typically is only about 30 seconds for Factor Xa. Use of acylation to prolong the half-life of certain blood factors has been disclosed. For example, Cassels, R. et al., *Biochem. Jour.* 247:359–400 (1987), reports that various acylating agents remained bound to urokinase, tPA and streptokinase-plasminogen activator complex for time periods ranging from a half-life of 40 minutes to a half-life of over 1,000 minutes depending on the nature of the acylating group and the nature of the factor. U.S. Pat. No. 4,337,244 describes acylation of tPA or streptokinase. Use of an amidinophenyl group functioning as an arginine analog to introduce, temporarily, a substituted benzoyl group into the active site for the purpose of enhancing serum stability was discussed by Fears, R. et al., *Seminars in Thrombosis and Homeostasis* 15:129–39 (1980) (see also: Fears, R. et al., *Drugs* 33 Suppl. 3:57–63 (1987); Sturzebecher, J. et al., *Thrombosis Res.* 47:699–703 (1987)), which describes stabilized acyl derivatives of tPA. Use of the acylated plasminogen streptokinase activator complex ("APSAC") is described in Crabbe, S. J. et al., *Pharmacotherapy* 10:115–26 (1990). Acylated forms of thrombin have also been described. Generally, methods for activating, inhibiting, and recovering the target blood factor have been multi-step and complex processes.

Chemically inactivated forms of Factor Xa can be used in a number of therapeutic indications (U.S. Pat. No. 4,285,932; U.S. Pat. No. 5,120,537; Benedict, C. R. et al, *Blood* 81 (8):2059–2066 (1993); U.S. Ser. No. 08/268,003, filed Jun. 26, 1994; Sinha, U. et al., "Procoagulation Activities of Reversibly Acylated forms of Factor Xa," presented at the 35th Annual Meeting of the American Heart Association, St. Louis, Mo., Dec. 3–7, 1993). Factor Xa can be irreversibly inactivated using chloromethyl ketone derivatives, such as glutamyl glycyl arginyl ("EGR") chloromethyl ketone, or dansyl glutamyl glycyl arginyl ("DEGR") chloromethyl ketone (see e.g.: Nesheim, H. E. et al., *Jour. Biol. Chem.* 254:10952 (1979); U.S. Pat. No. 5,120,537; Kettner, C. et al., *Biochem* 17(22):4778–4783 (1978); Kettner, C. et al., *Biochim. Biophys. Acta.* 569:31–40 (1979); Kettner, C. et al., *Arch. Biochem. Biophys.* 202:420–430 (1980); Kettner, C. et al., *Methods in Enzymology* 80 Part C:826–842 (1981); Kettner, C. et al., *Thromb. Res.* 22:645–652 (1981); Nesheim, M. E. et al., *J. Biol. Chem.* 256(13):6537–6540 (1981); U.S. Pat. No. 4,318,904; Lijnen, H. R. et al., *Thromb. Res.* 34:431–437 (1984); Williams, B., et al., *J. Biol. Chem.* 264(13):7536–7545 (1989); U.S. Pat. No. 5,153,175). This irreversibly inactivated Factor Xa can be used to inhibit thrombin generation in-vivo and thus be utilized as an anticoagulant (U.S. Pat. No. 5,120,537, and Benedict, C. R. et al. supra).

Factor Xa can be reversibly inactivated using various derivatives of 4-amidinophenyl benzoate (or p-amidinophenyl ester HCl) acylating compounds which impart reversibility at varying rates. This reversibly inactivated Factor Xa can be used to promote thrombin formation in vivo and thus can be utilized in procoagulant indications (U.S. Pat. No. 4,285,932; U.S. Ser. No. 08/268,003, filed Jun. 26, 1994; and Sinha et al., supra).

SUMMARY OF THE INVENTION

The invention features a process for producing a highly purified preparation of an inhibited (that is, inactivated permanently or transiently) form of an activated blood factor, by providing a partially purified preparation containing the blood factor, treating the partially purified preparation to convert the blood factor to an inhibited activated form in a single step (and/or in a single reaction vessel), and then purifying the resulting inhibited activated blood factor.

The invention provides for production of activated blood factors in permanently or transiently inhibited form, at high purity and in high yield. In certain embodiments, the methods of this invention can be used to prepare inhibited activated Factor II (inhibited Factor IIa), inhibited activated Factor V (inhibited Factor Va), inhibited activated Factor VII (inhibited Factor VIIa), inhibited activated Protein C, inhibited activated Protein S, inhibited activated Factor IX (inhibited Factor IXa), inhibited activated Factor X (inhibited Factor Xa), inhibited activated Factor XI (inhibited Factor XIa), inhibited activated Factor XII (inhibited Factor XIIa), and inhibited activated fibrinogen (inhibited Factor I).

The inhibition treatment can immediately follow the activating treatment, with or without an intervening process step, or, the activation and inhibition treatments can be carried out concurrently.

The partially purified preparation, containing the blood factor, can be derived from natural, synthetic or from recombinant source materials.

In some embodiments the inhibition treatment includes using a peptidyl chloromethyl ketone derivative, preferably being tri-peptidyl or greater, such as EGR-ck or DEGR-ck.

In some embodiments the inhibition treatment includes causing an acyl group to be bound at the active site of a blood factor (in activated or zymogen form), where it inhibits clearance and is susceptible to slow hydrolysis to generate the active form of the blood factor, resulting in a reversibly inhibited activated blood factor.

Other features and advantages will be apparent from the specification and claims.

DESCRIPTION OF SPECIFIC EMBODIMENTS

Definitions of Terms

As used herein, the terms "blood coagulation factor" and "blood factor" mean and refer to blood factors generally, and particularly to any of a number of peptides, factors and cofactors, which comprise the intrinsic or extrinsic blood coagulation cascade in humans, or are involved in modulation, localization or dissolution of blood clots. Blood factors suitable for use in this invention include, but are not limited to, Factors II, V, VII, IX, X, XI and XII, Proteins C and S, thrombin, fibrinogen, etc., in their zymogen, non-activated, activated or inhibited activated forms. The term "blood factor" refers to the respective native, synthetic or recombinantly produced polypeptide sequence as commonly known.

As used herein, the term "impure starting protein fraction" refers to any protein fraction either from natural, synthetic or recombinant sources which contains the blood factor of interest in combination with other proteins, or in combination with other materials present in the environment wherein the protein fraction was produced or derived.

The term "partially purified preparation" means a preparation that contains a blood factor of interest and that is substantially or completely free of inhibitors of the blood factor of interest. In certain embodiments, the partially purified preparation is substantially free of chelating agents or contains free calcium in molar excess of any chelating agents that may be present. A partially purified preparation may at be at a high level of purity.

Figure 1:
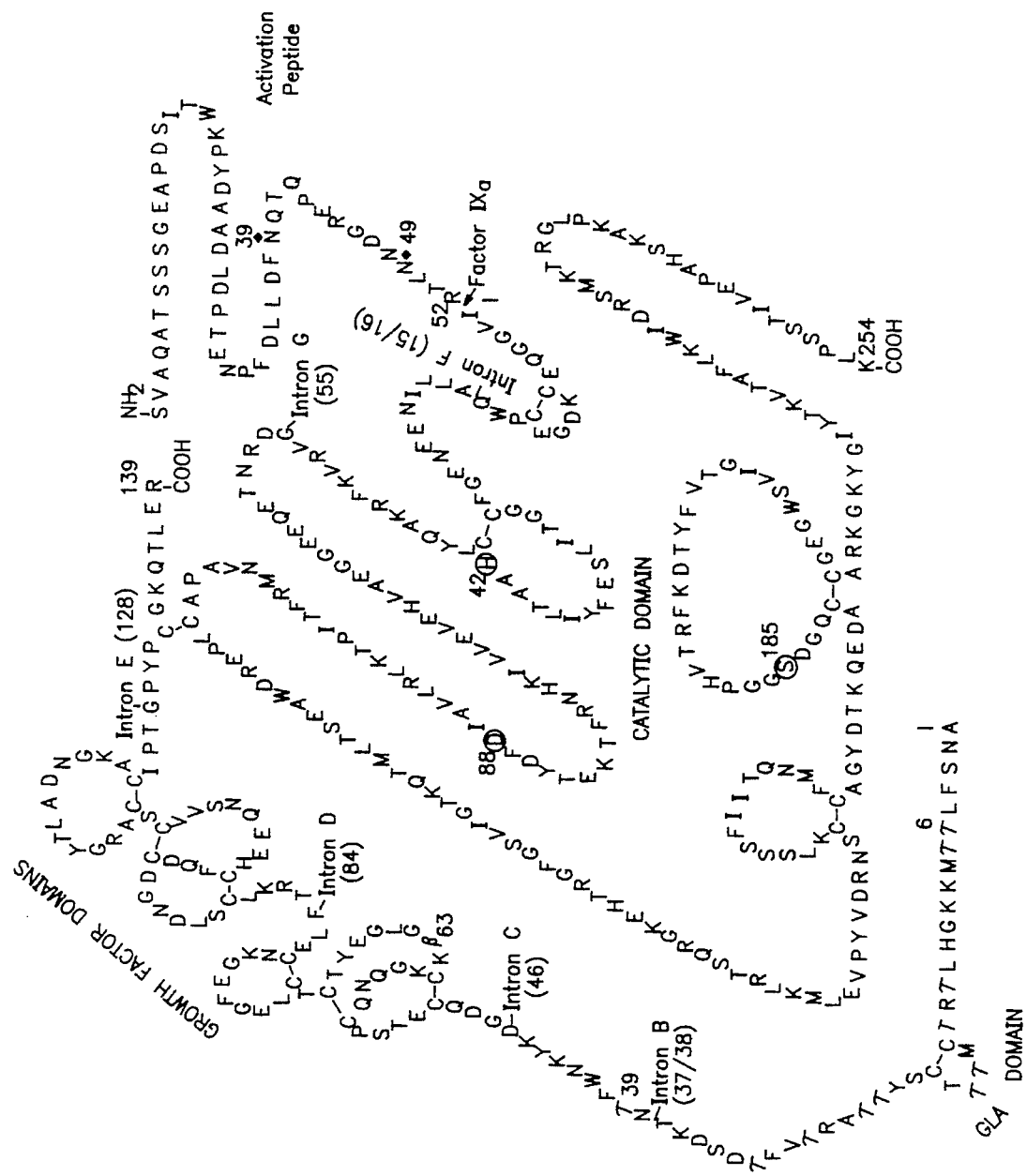
FIG. 1 (SEQ ID NO: 1 and SEQ ID NO: 2) is a schematic showing a human Factor X, indicating regions of the molecule.
Figure 2A:
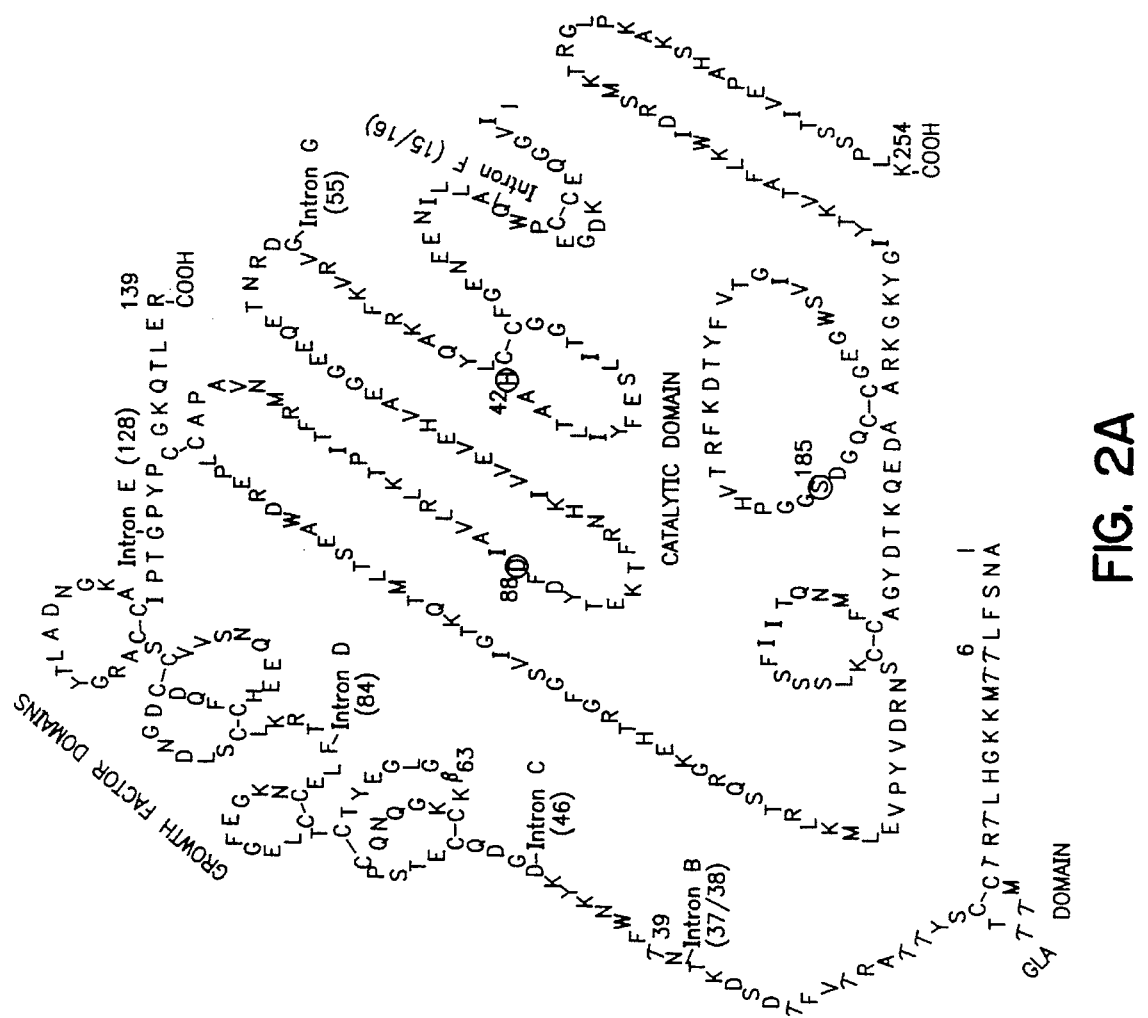
FIGS. 2A (SEQ ID NO: 3) and 2B (SEQ ID NO: 4) are schematics showing, respectively, a and β forms of a human Factor Xa.
Figure 2B:
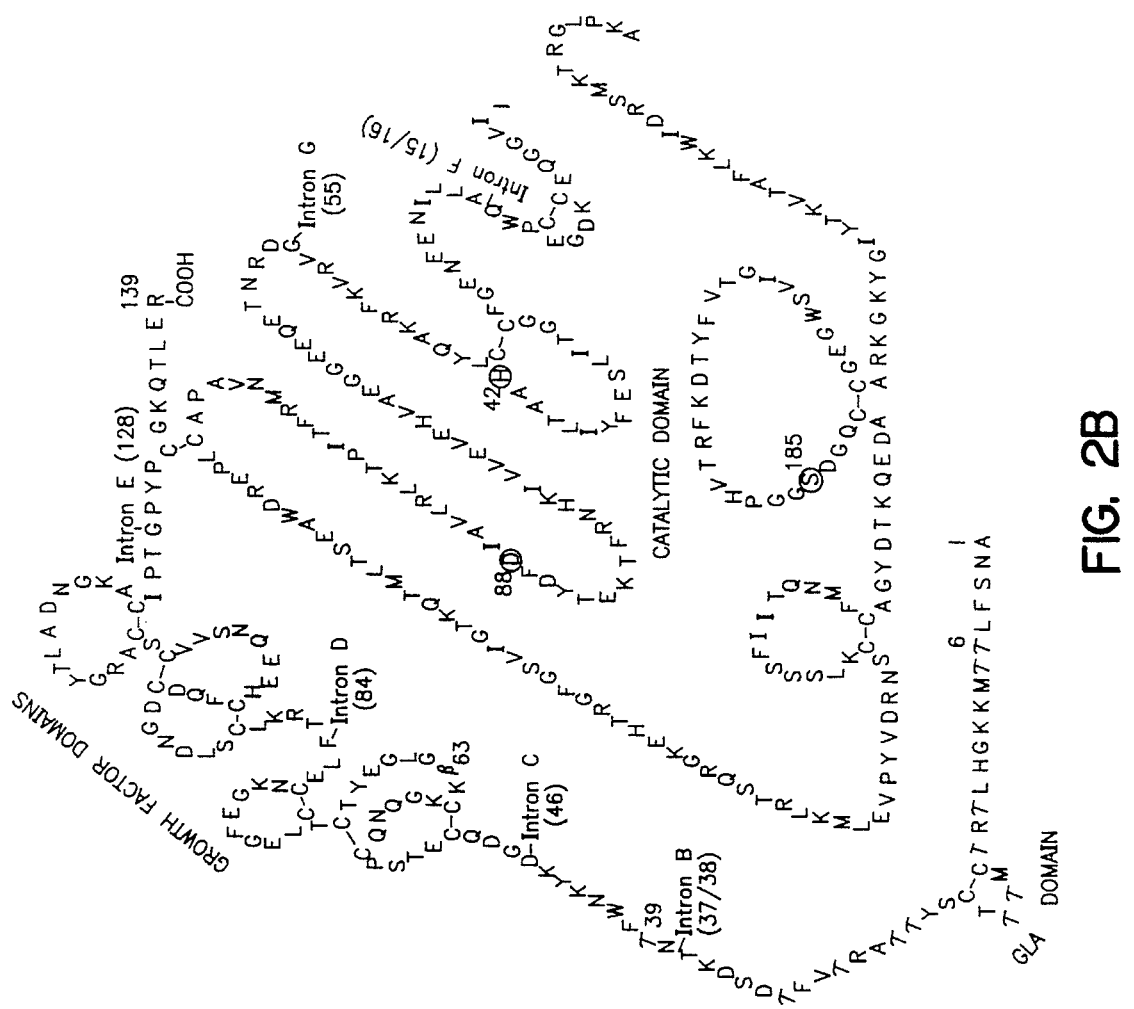

"Factor X" refers to the native, synthetic or recombinantly produced single- or two-chain Factor X sequence, essentially as shown in FIG. 1 or FIG. 2, containing at a minimum the heavy chain to which is attached the activation peptide, at its N-terminus, and the light chain. These may or may not be linked through a cleavage sequence as indicated in the figures.

"Factor IX", "Factor VII" and "Protein C" refer to the respective native or recombinantly produced protein sequence as commonly known.

The terms "chemical inhibitor" and "chemical inactivator", as used herein, mean and refer to any of a number of reactive peptidyl or organic molecules which have the ability to covalently bind to the active site of the activated blood coagulation factor and to render the activated blood coagulation factor inactive, that is, to inhibit the activity of the activated blood factor. Known reactive compounds include tri- (or greater-) peptidyl chloromethyl ketone derivatives or tri- (or greater-) peptidyl arginyl chloromethyl ketones to produce irreversibly inhibited compounds or any of a group of acylating agents which can produce transiently inhibited blood factors.

A blood factor that is "activated", as that term is used herein, is one that has been catalytically formed from an inactive zymogen precursor.

An activated blood factor that is "inhibited", as that term is used herein, is one that substantially lacks the enzymatic activity expected for the blood factor when activated.

"Factor Xa" refers to native, synthetic or recombinantly produced, enzymatically active Factor X containing light and heavy chain only. The activation peptide is not present in this complex.

"Inhibited Factor Xa" means and refers to a modified form of Factor Xa which is activated in the sense that it combines to form the prothrombinase complex, but which has no serine protease activity by virtue of the modification of its active site.

"Acylated Factor Xa" or "AcXa", unless otherwise specified, refers to Factor Xa, whether produced recombinantly or not, wherein the serine catalytic domain has been blocked with a substituent which provides the Acyl-Factor Xa with a half-life in serum of at least 5–10 minutes, preferably more than 15 minutes, and which releases Factor Xa in active form over this time period. The half-life in serum can be measured directly in vivo using a suitably labeled form. However, it is preferable to assess the ability of the extended life AcXa to generate the active factor Xa within the required time frame in vitro using as a criterion in vitro assays for which Xa is a catalyst. Under these conditions, suitable forms of Acylated Factor Xa for the invention include those which have a rate constant for hydrolysis in isotonic aqueous media at pH 7.4 and 37° C. such that a half-life of approximately 5 minutes to several hours is achieved. The half-life can be determined directly in vitro by measuring the rate of hydrolysis of the acylated Xa, if desired, using its ability to activate clotting, or the prothrombinase reaction as criteria for Xa formation.

The blood factors described in this invention are defined herein to be any isolated polypeptide sequence which possesses a biological property of the naturally occurring blood factor polypeptide comprising a commonly known polypeptide sequence, variants and homologues thereof, and mammalian or other animal analogues.

"Biological property" for the purposes herein means an in vivo effector or antigenic function or activity that is directly or indirectly performed by a blood factor (whether in its native or denatured conformation), or by any subsequence thereof. Effector functions include receptor binding, any enzyme activity or enzyme modulatory activity, any carrier binding activity, any hormonal activity, any activity in promoting or inhibiting adhesion of cells to an extracellular matrix or cell surface molecules, or any structural role. However, effector functions do not include antigenic functions, i.e., possession of an epitope or antigenic site that is capable of cross-reacting with antibodies raised against a naturally occurring blood factor polypeptide.

Ordinarily, the blood factors claimed herein will have an amino acid sequence having at least 75% amino acid sequence identity with a commonly known sequence, most preferably at least 80%, even more preferably at least 90%, and most preferably at least 95%. Identity or homology with respect to a commonly known blood factor sequence is defined herein as the percentage of amino acid residues in the candidate sequence that are identical with the known blood factor amino acid residues, after aligning the sequences and introducing gaps, if necessary, to achieve the maximum percent homology, and not considering any conservative substitutions as part of the sequence identity. None of N-terminal, C-terminal or internal extensions, deletions or insertions into the blood factor sequence shall be construed as affecting homology.

Thus, permanently or transiently inactivated blood factor polypeptides and blood factors with extended plasma half-lives that can be made according to this invention include each blood factor sequence; fragments thereof having a consecutive sequence of at least 5, 10, 15, 20, 25, 30 or 40 amino acid residues from a commonly known blood factor sequence; amino acid sequence variants of a commonly known blood factor sequence wherein an amino acid residue has been inserted N- or C-terminal to, or within, the blood factor sequence or its fragment as defined above; amino acid sequence variants of the commonly known blood factor sequence or its fragment as defined above has been substituted by another residue. Blood factor polypeptides include those containing predetermined mutations by, e.g., site-directed or PCR mutagenesis, and other animal species of blood factor polypeptides such as rabbit, rat, porcine, non-human primate, equine, murine and ovine blood factors, and alleles or other naturally occurring variants of the foregoing and human sequences; derivatives of the commonly known blood factor or its fragments as defined above wherein the blood factor or its fragments have been covalently modified by substitution, chemical, enzymatic or other appropriate means with a moiety other than a naturally occurring amino acid (for example, a detectable moiety such as an enzyme or radioisotope); glycosylation variants of the blood factor (insertion of a glycosylation site or deletion of any glycosylation site by deletion, insertion or substitution of appropriate amino acid); and soluble forms of the blood factor.

MODES OF CARRYING OUT THE INVENTION

General

As summarized above, this invention provides a process for producing large-scale quantities of chemically inactivated (i.e., chemically inhibited) activated blood factors from an impure starting protein fraction. Generally, the process includes one or more steps to obtain a partially purified preparation containing the blood factor of interest; the step of treating the partially purified preparation to activate and inhibit the blood factor; and steps to complete the purification of the resulting inhibited activated blood factor. The inhibition treatment can immediately follow the activating treatment, with no intervening process step; or, the activation and inhibition treatments can be carried out concurrently.

Figure 3:
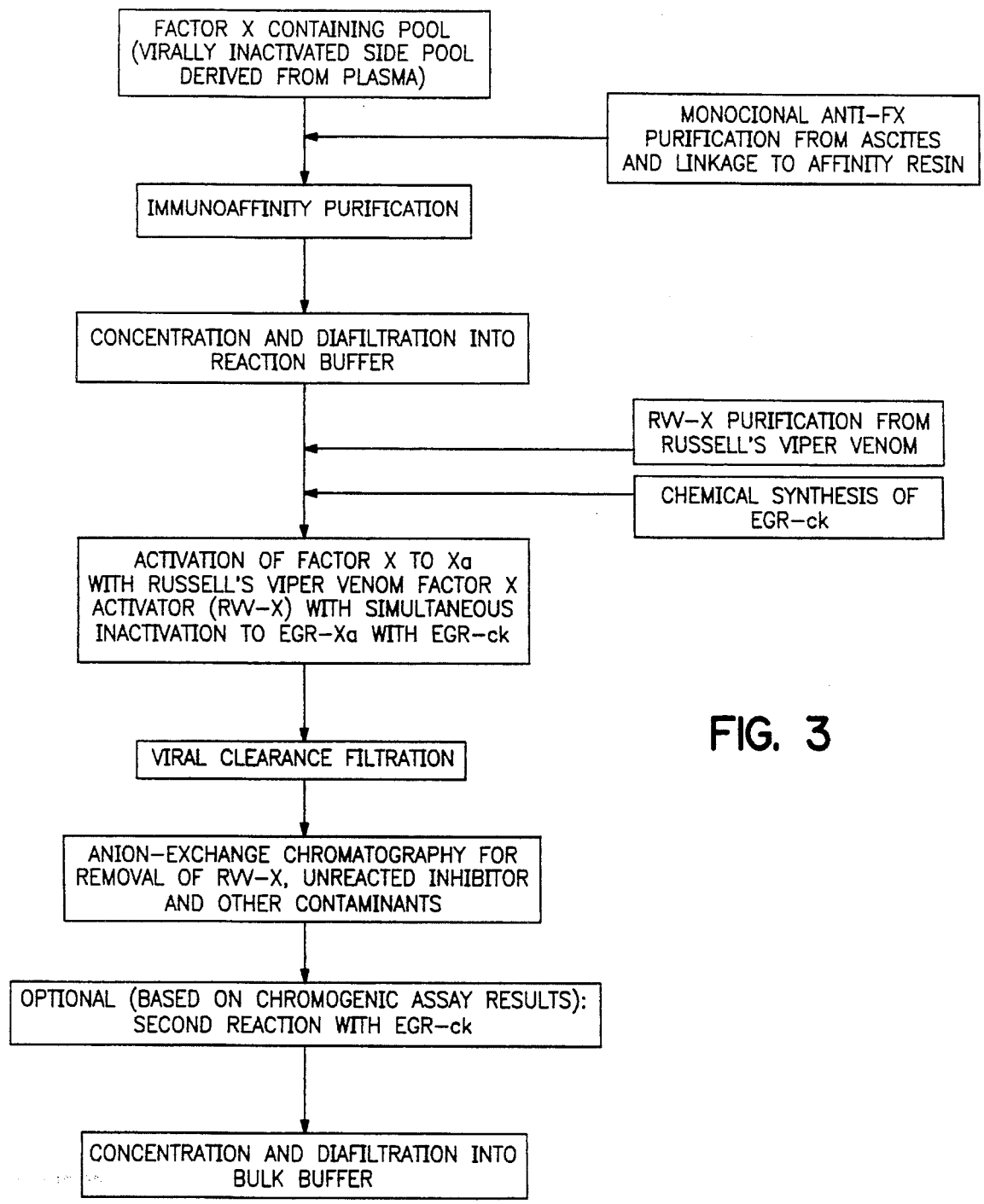
FIG. 3 is a schematic block diagram showing process steps according to an exemplary embodiment of the invention for producing an inhibited activated blood factor.

FIG. 3 shows a block diagram outlining a preferred embodiment of the process of this invention for producing irreversibly or reversibly inhibited forms of blood coagulation factors, with specific reference to Factor X inactivated with EGR-ck.

Referring to the preferred embodiment exemplified in FIG. 3, the starting matedal is a plasma fraction, preferably virally inactivated, containing the blood factor of interest. The starting material may alternatively be a product of recombinant expression of the blood factor. The starting material may be initially processed, for example through an affinity purification chromatography column (e.g., an immunoaffinity column), to produce the partially purified preparation containing the blood factor of interest. As shown in FIG. 3, a highly specific affinity purification step is used, so that the resulting elution pool contains the desired blood coagulation factor at a high level of purity.

The partially purified preparation may then be concentrated and/or diafiltered into a buffer suitable for carrying out the activation and inactivation (inhibition) treatments. In FIG. 3, the blood factor of interest is Factor X, which can be activated using RVV-X, purified from the venom of *Vipera russelli*, to produce Factor Xa; and Factor Xa can be inactivated using a peptidyl chloromethyl ketone or an acylating agent. Here, the preparation is treated concurrently with RVV-X and EGR-ck, to produce EGR-Factor Xa.

Thereafter a series of final purification steps is carried out to bring the inhibited activated blood factor of interest to a desired level of purity. Particularly, as in the example in FIG. 3, the treated preparation may subjected to a further viral clearance step, an ion exchange step to remove various contaminants and, optionally, an additional inactivation step (here using EGR-ck) to sweep up substantially all remaining activated factor. The product may then be concentrated and diafiltered into a storage buffer.

Partial Purification of Source Material Containing the Blood Factor

Any of a variety of techniques and combinations of techniques, known in the art, may be used to partially purify the preparation to make it ready for activation and inhibition treatment. Preferably the partially purified preparation contains substantially no inhibitors of the blood factor of interest; and preferably it contains no blood coagulation factors other than the factor of interest, although other zymogen factors may be present. For example, where Factor X is the blood factor of interest, and Russell viper venom (RVV-X) is used as an activating agent, the partially purified preparation should be substantially free of Factors V and IX, as Factors V and IX are also subject to activation by RVV-X. Where the blood factor is calcium-dependent, the use of chelators should avoided, unless free calcium is present in a molar excess of the chelator. For this reason, EDTA and EGTA buffers are less preferred.

Preferably (for improved yield), although not necessarily, the blood factor of interest is present in the partially purified preparation at about 50% purity, more preferably at about 80% purity, and still more preferably at about 90% purity. Preferred techniques for partial purification include, for example, column chromatographic techniques using immunoaffinity, heparin-affinity, and hydroxylapatite, sulfated dextrans, ion-exchange chromatography, metal-chelate chromatography, sulfated non-carbohydrate matrices, Cohn fractionation, hydrophobic interaction chromatography ("HIC"), and ammonium sulfate precipitation. DEAE resins are suitable, and preferably (although not necessarily) anion exchange chromatography can be used, also preferred are any of various quaternary amine columns can be used, e.g., the "Q" columns.

In certain preferred embodiments, an immunoaffinity resin is prepared and used according to generally accepted methods in the field. Preferred resins include Tresyl-activated Agarose, under the registered trademark Affinica® from Schleicher and Scheull, as well as other Tresyl activated resins, Aldehyde activated resins, Triazine activated resins, Hydrazide activated resins, Azlactone activated resins, and others. Typically, using standard techniques, a hybridoma cell line producing a monoclonal antibody with specificity for the target blood factor is obtained. The cell line is then injected into mice in order to conveniently produce quantities of the monoclonal antibody in ascites fluid, however recombinant production or other antibody/ antibody fragment production techniques may advantageously be utilized.

The monoclonal antibody may then be chromatographically purified using standard techniques such as protein A and ion-exchange chromatography techniques to greater than 98% purity. The required amount of resin may be prepared according to the manufacturer's instructions and both the resin and antibody may then be buffer exchanged into the coupling buffer. In a preferred embodiment, the coupling buffer contained 0.1M sodium carbonate at pH 8.5, and the antibody solution was incubated overnight with the Tresyl-activated resin at 2°–8° C. to allow efficient antibody coupling. The antibody can be coupled to the resin according to methods known in the art, commonly at ratios of between 1–10 mg antibody per milliliter of resin. After the coupling step, the linked resin is washed and blocked, typically according to manufacturer's instructions, and packed into an appropriate chromatography column (either radial or axial flow geometries) for use in the purification of the blood factor of interest.

In a particularly preferred embodiment, an anti-Factor X immunoaffinity column is set up using an immunoaffinity resin made as described above and used to partially purify a plasma fraction containing Factor X as the blood factor of interest. A frozen Factor X containing plasma fraction (e.g., a Factor IX affinity chromatography column wash fraction, or a DEAE or calcium phosphate eluate from a plasma fractionation process, Cohn fraction, etc.) is obtained; the plasma fraction may have been heat or solvent-detergent treated to reduce potential viral load and pH adjusted to neutral pH±0.5 units. The plasma fraction is thawed to between 2° and 8° C., 0.2 μm filtered and applied to an anti-Factor-X immunoaffinity column equilibrated with phosphate buffered saline solution at 2°–8° C. The residence time of the load through the column is set to be greater than or equal to 5 minutes. Once an appropriate load for the binding capacity of the column (generally 0.1–1.0 mg antigen/ml resin) has been applied, the column is washed with a volume of phosphate buffered saline equal to at least 10 column volumes. After sufficient column washing, the purified antigen, Factor X, is eluted using 0.1M CAPS buffer containing 25 mM sodium chloride, pH 10.5–11.3. The elution pool which is >90% Factor X is immediately titrated to neutral pH±0.5 units with concentrated (2–3M) HEPES buffer.

The Activation and Inhibition Step

In the activation and inhibition step, an inhibition (inactivation) treatment is carried out concurrently with an activation treatment; or an inactivation treatment follows an activation treatment with or without intervening processing steps. Techniques for activating and inactivating any of the various blood factors are known in the art and are discussed above by way of background.

Irreversible Inactivation

Generally, irreversible inactivation may be accomplished by any of a variety of methods discussed above, including irreversible inactivation by chloromethyl ketone derivatives, or by using small molecules which covalently and irreversibly bind to the active site of the blood factor.

In particularly preferred embodiments, a preparation containing Factor X, purified as described above, can be treated to activate and inhibit the Factor X as follows. The purified Factor X is concentrated to approximately 1 mg/ml utilizing a Filtron ultrafiltration system with 8 kDa MWCO Omega type membranes, or another equivalent system. The concentrated Factor X can then be diafiltered into 50 mM Tris buffer, 25 mM sodium chloride, pH 7.5 or can be directly activated, without buffer exchange, using Russell's Viper Venom Factor X activating enzyme (RVV-X) at a mass:mass ratio of Factor X:RVV-X of between 1000:1 to 20:1 at 18°–37° C. in the presence of 5 mM calcium chloride for at least 5–10 minutes. Purified RVV-X can be prepared through a number of previously published processes (Williams, W. J. et. al, *Biochem. J.* 84:52–62 (1962); Kisiel, W. et al., *Biochem.* 15(22):4901–4906 (1976); and Takeya, H. et al., *J. Bio. Chem.* 267(20):14109–14117 (1992)) from crude RVV. The reaction may be stopped after one hour with the addition of EDTA to 10 mM. The activated Factor X (Factor Xa) can be either simultaneously or sequentially reacted with a covalent inhibitor, either a tripepride chloromethyl ketone or acylating agents (e.g., variants of 4-amidinophenyl benzoate or others as discussed below), at a molar ratio of greater than 20:1 inhibitor:Factor X for at least 30 minutes at room temperature in order to inactivate (that is, to inhibit) the Factor Xa.

Reversible Inactivation

Techniques for irreversibly and reversibly inactivating activated blood factors are disclosed in copending U.S. patent application Ser. No. 08/268,003, filed Jun. 29, 1994, the pertinent parts of which are hereby incorporated by reference. Generally, reversible (that is, transient) inactivation may be accomplished by any of a variety of methods, including binding of an antibody/antibody fragment to the active region, binding of moiety which blocks sterically the proteolytic or other active domain, or incorporation of a chemical moiety which blocks the active blood factor domain and gradually is released from the blood factor. In particularly preferred embodiments of this invention the blood factor is transiently inactivated by being acylated.

Reversible inactivation may be accomplished using benzamidines, which are good reversible inhibitors of trypsin-like enzymes. The cationic amidino group of the inhibitor interacts with an enzyme carboxylate located at the bottom of the S1 subsite. A wide variety of substituted benzamidines have been investigated as inhibitors of thrombin and plasmin and are suitable for practice of this invention (see, e.g., Andrews, J. M. et al., *Jour. Med. Chem.*, 21:1202–07 (1978)). Extensive studies have been reported on compounds containing two benzamidine moieties, which are also desirable for the practice of this invention (see, e.g., Tidwell, R. R. et al., *Thrombosis Research* 19:339–49 (1980)). 1,2-bis(5-amidino 2-benzofuranyl) ethane is also useful for transient inhibition, and is known to inhibit Factor Xa with a Ki of 570 Nm.

Also suitable for transient inactivation in the activation/ inhibition step according to the invention are Kunitz inhibitors (a class of widely studied protease inhibitors). Bovine pancreatic trypsin inhibitor (aprotinin) and tissue factor pathway inhibitor (also known as LACI) belong to this class. Dissociation constants (T) can range from 17 weeks to 11 seconds (Gebhard, W. et al., *Proteinase Inhibitors*, (1986) Elsevier). Aprotinin competitively inhibits factor VIIa with a Ki of 30 uM (Chabbat, J. et al., *Thrombosis Research*, 71:205–15 (1993)).

Treatment to inhibit activated blood factors by acylation according to the invention, proceeds by standard acylation reaction of the corresponding blood factor, whether recombinantly produced or isolated from plasma, according to procedures analogous to those set forth, for example, or referenced in, Cassels, R. et al., *Biochem. Jour.*, 247:395–400 (1987), or U.S. Pat. No. 4,337,244.

In certain embodiments in the activation/inhibition step according to the invention, the partially purified preparation containing the blood factor is treated with a three to thirty-fold molar excess of an acylating agent in a neutral pH buffer at room temperature. Catalytic activity is followed over a time course of approximately one to sixty, and preferably for ten to thirty minutes to assure the desired level of inactivation of protein. The reagent is preferably prepared as a 0.1M solution in DMSO or water and added to the protein at pH 7.5. Blocked protein is subjected to chromatography (preferably on a gel-filtration or ion-exchange column) at pH 5.0 to remove excess reagent. Protein may be stored at pH 5.0 at −70° C. to −80° C. prior to further use.

Suitable active site acyl groups for use in this invention include benzoyl, p or o methyl (toluoyl), p or o methoxy (p is a more preferred anisoyl), p or o fluoro benzoyl, Dimethyl acryloyl (3,3 or 3,4), Difluoro compounds, $CH_3$ CO benzene (acetyl gp), $CH_3$ CO NH benzene (acetanilide), p or o ethoxy (or other alkyl groups), and guanidino benzoyl.

Suitable esters for use in this invention include the 4-toluoyl ester, the 3,3-dimethyl acrylyl ester, cyclohexylidineacetyl ester, the cyclohex-1-enecarbonyl ester, the 1-methylcyclohexylidineacetyl ester, the 4-aminobenzoyl ester, the p-anisic acid p-amidinophenyl ester, the o-anisic acid p-amidinoophenyl ester, the 3,4 dimethyl benzoic acid p-amidinophenyl ester, the benzoic acid p-amidinophenyl ester, the 3,3 dimethylacrylic acid p-amidinophenyl ester, and the PDAEB (4-N-(2-N'-(3-(2-pyridyldithio)-propenyl)aminoethyl) amino benzoyl ester. In general, the acylating agent will be the activated form of a non-toxic acid which provides a saturated, unsaturated or aromatic 5- or 6-carbon ring to which a carboxyl is substituted. The ring may contain further substitutions, such as amino, alkoxy, alkyl, addition ring systems, or any other non-interfering non-toxic substituent. For Factor X and other blood factors having a catalytically active serine domain, any compound capable of acylating the serine hydroxyl group or otherwise blocking the serine catalytic domain in a reversible manner is suitable for synthesis of the acylated blood factor. As described in U.S. Pat. No. 4,337,244, in general, either direct or inverse acylating agents can be used. For direct acylating agents, the acylating moiety is itself attracted to the catalytic site of the Factor Xa or other blood factor; in the inverse acylating approach, the leaving group is thus attracted. The acylated form of the blood factor is then purified from the reaction mixture using standard purification techniques, including dialysis, chromatography, selective extraction, and the like.

Potent acylating agents such as 3-alkoxy 4-chloroisocoumarins have been reported for a variety of serine proteases (Harper, J. W. et al., *Jour. Am. Chem. Soc.*, 106:7618–19 (1984); Harper, J. W. et al., *Biochemistry*, 24:7200–13 (1985)), and are suitable for use in the activating/inhibiting step according to the invention. The stability of the acyl enzymes are dependent on the alkoxy groups, small groups giving transiently stable (T<2h) acyl enzymes.

The compounds produced according to the processes of this invention which serve as acylated blood factor diagnostics and/or pharmaceuticals must have an appropriate deacylation rate which assures an appropriate clearance time in vivo. The acylated proteins reactivate in a time, temperature and pH dependent manner. Typically, deacylation is faster at 37° C. than at room temperature, and is faster at pH 8.0 than at pH 7.5. The deacylation rate can be measured as having a half-life of at least 5 minutes in vitro in buffer using prothrombinase and/or clotting assays. Deacylation can be measured directly as described in R. A. G. Smith et al., *Progress in Fibrinolysis*, Vol. VII, pp. 227–31 (1985, Churchill Livingstone). Prothrombinase and clotting assays are described in D. L. Wolf et al., *Jour. Biol. Chem.*, 266:13726 (1991).

In certain preferred embodiments, deacylation of acyl Factor Xa is carried out by incubation in a solution of appropriate pH and assaying aliquots in an amidolytic or clotting assay. The relative activity is calculated as a percentage of equivalent amount of active Factor Xa carried through the same incubations. The preferred assay for acyl Factor VIIa involves multiple steps. The acyl enzyme is incubated in the appropriate buffer at a protein concentration of 160 nM. At each time point, an aliquot is diluted to 0.16 nM and incubated with lipidated tissue factor (0.25 nM) for 1 min at room temperature. The factor VIIa/Tissue Factor mixture is then used for activation of Factor X and resulting Factor Xa assayed in an amidolytic assay.

Purification Following the Activation and Inhibition Step

Following the step of treating the partially purified preparation to activate and inhibit the blood factor, any of a variety of subsequent purification techniques and combinations of techniques, known in the art and such as those discussed above, can be used to bring the inhibited activated blood factor to a final acceptable degree of purity.

In a particularly preferred embodiment, the product resulting from the activation and inhibition step described above, namely inhibited Factor Xa, is ultrafiltered at ambient temperature using a Millipore Viresolve™ unit or equivalent process to further remove potential contaminants (e.g., viruses, IgG, RVV-X, Factor X, etc.). For a standard one square foot Millipore Viresolve™ membrane unit, for example, typically the cross flow rate is maintained at between 1.0–1.7 liter/minutes, while the permeate rate is controlled at between 5–60 ml/min. A one square foot Viresolve™ unit has enough membrane capacity to filter at least one gram of Inhibited Factor Xa at a concentration of approximately 0.7±0.3 mg/ml, however other parameters are suitable for the practice of this invention. In order to achieve enhanced product recovery, after filtration is completed, the system should be rinsed more than two, and preferably at least five times with at least 75 ml each time using the appropriate buffer used in the reaction, pH 6.0–7.5 (although it must be recognized that other buffers, volumes and timing may be desired for a particular application).

The resulting permeate may then be directly loaded at ambient or other convenient temperature onto an anion exchange or other chromatography column. In this particularly preferred embodiment, a DEAE Fractogel resin is utilized with a loading capacity of at least 8 mg product per ml of resin. When working with permanently inactivated compounds, the column is preequilibrated with phosphate buffer at pH 6.5 (or pH 5.0–5.5 for reversibly inactivated compounds) containing less than 0.2M sodium chloride. The sample mass appropriate to the column loading capacity is applied and once application is complete, the column is washed with at least 5 column volumes of phosphate buffer at pH 6.5 (or pH 5.0–5.5) containing no sodium chloride. A step change is made to wash the column with at least 5 column volumes of phosphate buffer at pH 6.5 (or pH 5.0–5.5) containing 0.2M sodium chloride. The product is then eluted with a step change to phosphate buffer at pH 6.5 (or pH 5.0–5.5) containing 0.3M sodium chloride.

If desired, the elution pool from the DEAE Fractogel column (or other purification step) can be incubated with the inhibitory agent a second time in order to reduce the level of residual Factor Xa (or other blood factor) which may co-purify with the Inhibited Factor Xa (or other blood factor).

The elution pool from the DEAE Fractogel column (or second inactivation step) may then be concentrated and diafiltered if desired into the final storage buffer of choice using for example a Filtron ultrafiltration system with 8 kDa MWCO Omega type membranes.

Therapeutic and Other Uses of the Blood Factors

When used in vivo for therapy, the blood factors of the subject invention are administered to the patient in therapeutically effective amounts (i.e. amounts that have desired therapeutic effect). They will normally be administered parenterally. The dose and dosage regimen will depend upon the degree of the coagulation disorder, the characteristics of the particular activated or inhibited blood factor used, e.g., its therapeutic index, the patient, and the patient's history. Advantageously the blood factor is administered in an acute care setting, or continuously over a period of 1–2 weeks, or over a number of years intravenously to treat disorders in vasculature function. Optionally, the administration is made during the course of adjunct therapy such as angiography, angioplasty, thrombolysis, stent placement, heart/valve/artery/venous surgery or transplant, combined cycles of pro- or anti-coagulant therapies including platelet aggregation inhibitors, or as part of therapeutic administration of other cardiovascular modulatory agent.

For parenteral administration the blood factors will be formulated in a unit dosage injectable form (solution, suspension, emulsion) in association with a pharmaceutically acceptable parenteral vehicle. Such vehicles are inherently nontoxic, and non-therapeutic. Examples of such vehicles are water, saline, Ringer's solution, dextrose solution, and 5% human serum albumin. Nonaqueous vehicles such as fixed oils and ethyl oleate can also be used. Liposomes may be used as carriers. The vehicle may contain minor amounts of additives such as substances that enhance isotonicity and chemical stability, e.g., buffers and preservatives. The blood factors will typically be formulated in such vehicles at concentrations of about 0.1 mg/ml to 100 mg/ml.

The blood factor compositions used in therapy are formulated and dosages established in a fashion consistent with good medical practice taking into account the disorder to be treated, the condition of the individual patient, the site of delivery of the composition, the method of administration and other factors known to practitioners. The blood factor compositions are prepared for administration according to the description of preparation of blood factors, infra.

EXAMPLES

The Examples that follow illustrate the invention by specific reference to production of Inhibited Factor X. The Examples are intended to be illustrative only, and do not limit the scope of the invention.

EXAMPLE 1

Preparation of Immunoaffinity Resin

In one example of the practice of this invention for the preparation of an anti-Factor X immunoaffinity column, anti-Factor X monoclonal antibody, from crude mouse ascites, was purified via protein A, S-Sepharose Fast Flow and DEAE Fast Flow chromatography in sequential steps and was then buffer exchanged into 0.1M sodium carbonate buffer, pH 8.5 in preparation for linkage to Tresyl-activated Agarose (Schleicher and Schuell). 5 liters of antibody solution at 2 mg/ml was linked for no less than 12 hours at 4° C. to an equal volume of prepared Tresyl-activated resin. The mixture was continuously agitated in order to maintain optimum contact between the resin and the antibody solution. After coupling, the supernatant was recovered from the resin slurry and assayed by an absorbance measurement for protein concentration. The resin was then incubated for at least 12 hours at 4° C. with 0.1M Tris buffer, pH 8.5, in order to block the remaining unreacted Tresyl sites on the activated resin. After blocking, the supernatant was again collected and assayed by an absorbance measurement. The resin was then washed with 10 resin volumes of 20 mM Potassium phosphate buffer at pH 7.0 containing 1.0M sodium chloride. The high salt wash was also collected and assayed for absorbance. The antibody binding efficiency of the process was determined to be greater than 98% when calculated taking the difference between the known amount of antibody in the initial mixture and the mass of antibody recovered in the sum of the supernatant samples and then dividing by the initial starting mass of antibody. Antigen dynamic binding capacity was determined by packing a one milliliter column of the coupled resin and applying Factor X to the column after it had been equilibrated with phosphate buffered saline. The Factor X was then eluted with 0.1M CAPS buffer, pH 10.5 and neutralized with 2M HEPES to pH 7.5 for absorbance measurement. The dynamic Factor X binding capacity was determined to be at least 0.1±0.2 mg Factor X per milliliter of resin.

EXAMPLE 2

Partial Purification of Factor X from a Natural Plasma Source

In one example of practice of this invention for purification of Factor X from a natural plasma source using an anti-Factor X immunoaffinity column, a 50 ml sample from the wash fraction of a Factor IX affinity purification step containing approximately 2.2 mg total protein per ml (based on a dye-binding total protein assay) of which 50% of the total protein was Factor X was directly applied to a 100 ml radial flow column containing anti-Factor X linked to Tresyl-activated Agarose pre-equilibrated with phosphate buffered saline. The load sample was applied at a flow rate of 20 ml per minute to provide a residence time of at least 5 minutes. After the flow through peak returned to baseline by washing with phosphate buffered saline, the column was then washed with phosphate buffered saline containing 0.5M sodium chloride for at least 3 column volumes. The Factor X was then eluted with 0.1M CAPS buffer containing 0.025M sodium chloride at pH 10.5 in approximately 2.5 column volumes. The elution pool was assayed by absorbance measurement, total protein assay, and SDS-PAGE. The analysis showed that the elution pool is predominantly a single band, with no detectable major contaminant bands and that less then 15% of the Factor X loaded flowed through the column when the column was loaded to at least 67% of capacity.

EXAMPLE 3

Activation and Inhibition of Factor X and Anion Exchange Chromatography of Reaction Mixture In one example of practice of this invention for the conversion of factor X to the inhibited form of Factor Xa and the subsequent purification, 11 mg of immunoaffinity purified Factor X were reacted at ambient temperature for one hour with EGR-ck (Peptisyntha, Belgium; EGRock obtained from Calbiochem, San Diego, Calif.; from Bachem, Torrance, Calif.; or from Bachem AG, Switzerland have performed similarly) and RVV-X (Haemtech, Burlington, Vt.; RVV-X obtained from ERL, Indianapolis, Ind. has performed similarly) at a molar ratio of 20:1 EGR-ck:Factor X and at a mass ratio of 1:250 RVV-X:Factor X, respectively, in the presence of 5 mM calcium chloride. The RVV-X reaction was stopped by the addition of concentrated EDTA to 10 mM. The reaction mixture was analyzed by Size Exclusion HPLC and a chromogenic assay specific for Factor Xa. The results showed that the reaction converting Factor X to Factor Xa had proceeded to greater than 80% conversion, and that the residual Factor Xa was less than 400 nanogram per milliliter of solution.

The reaction mixture was then directly applied to a 1.2 ml DEAE column (Fractogel 650M, E. Merck, Darmstadt, FRG; other anion exchange resins, e.g., A Fast Flow and DEAE Fast Flow, obtained from Pharmacia, Uppsala, Sweden; Poros Q, Poros PEI, Poros IIQ, obtained from Perceptive Biosystems, Boston, Mass.; etc., have performed similarly) pre-equilibrated with 20 mM sodium phosphate buffer, pH 6.5, containing 0.2M sodium chloride. The flow through was washed to baseline with 20 mM sodium phosphate buffer, pH 6.5, and then the column was washed with at least 5 column volumes each of 20 mM sodium phosphate buffer, pH 6.5, containing 0.15M, 0.2M and 0.25M sodium chloride. The Inhibited Factor Xa was eluted with a step to 0.3M sodium chloride in 20 mM sodium phosphate buffer, pH 6.5, in a total of 8 column volumes. The column was then washed with a high salt solution, 1.0M sodium chloride and then stripped with 0.5N sodium hydroxide. Total protein assays and SDS-PAGE were performed on all eluted fractions along with Size Exclusion HPLC, Reversed-phase HPLC and contaminant ELISA's on the elution pool. The HPLC results indicated that the elution pool was greater than 89% pure by both HPLC methods. The total protein recovery of the step resulted in a 97% mass balance, indicating good recovery of all protein loaded onto the column. The contaminant assays indicated that the DEAE step was able to clear contaminants such as anti-Factor X IgG and RVV-X at levels at least 500-fold. Additionally, the SDS-PAGE gels indicated that many contaminating bands had been removed from the load sample during the flow through and wash steps prior to elution. This result indicates that the DEAE binding capacity for Inhibited Factor Xa was at least 6 milligrams of Inhibited Factor Xa per ml of resin.

EXAMPLE 4

Ultrafiltration of Reaction Mixture using Millipore Viresolve™

In one example of practice of this invention for the ultrafiltration of the reaction mixture, a 70 kDa NMWCO small area module (Millipore, Viresolve™ 70, containing 0.01 ft$^2$ membrane area) was used. Factor X (14.5 ml at 0.5 milligram per ml, or 29 mg), was reacted with RVV-X and EGR-ck as described in Example 3 above. The reaction mixture was then recirculated over the small area module at a cross flow rate of 12 ml per minute with a peristaltic pump for 30 minutes to equilibrate the system. Several permeate flow rates, ranging from 0.15 to 1.0 ml per minute, were collected and tested by absorbance measurement at 280 nm. All permeate flow rates exhibited greater than 90% passage of protein when a representative permeate sample was collected. Thus, for scale-up purposes, a volume reduction experiment was conducted to examine total protein recovery upon passage of a fixed quantity of protein. A total protein recovery of greater than 80% was achieved with no wash steps incorporated. Additional wash steps may be included if desired to increase recovery. This experiment showed that per square foot of membrane area, at least one gram of total protein (at a concentration of 0.5 mg per ml) from the reaction mixture was processed with greater than 80% recovery in a time between one-half hour and one hour.

EXAMPLE 5

Large-scale Production of Highly Purified EGR-Factor Xa: Preparation of Immunoaffinity Resin Examples 5 through 10 illustrate a process according to this invention for the large-scale production of highly purified EGR-Factor Xa. Although each of these examples stand independently, they may also be understood as processes which occurred sequentially, with the product from each of Examples 5 through 9 being used for the steps described in the following example.

To prepare an immunoaffinity resin specific for Factor X, ten grams of a highly purified ascites-derived murine monoclonal anti-Factor X antibody was coupled to 2.2 liters of Actigel™ ALD low substitution monoaldehyde activated resin (Sterogene, Arcadia, Calif.). The coupling reaction was carried out in an 180 mm Moduline™ column (Amicon, Beverly, Mass.), in 0.1M sodium phosphate buffer, 0.1M sodium cyanoborohydride, pH 7.0, for 20±4 hours at 2°–8° C. The mixture was maintained as a homogeneous slurry through the use of continuous agitation with an overhead mixer. After coupling, the resin was allowed to settle and the column effluent collected and assayed for the presence of antibody. Less than 5% of the original antibody was detected in the supernatant by an absorbance measurement at 280 nm. The resin was then washed with 20 liters of 0.1M sodium phosphate buffer, 0.5M sodium chloride, pH 7.0 to remove non-specifically bound protein. The remaining unlinked monoaldehyde linkage sites were blocked by recirculating 0.1M Ethanolamine, 0.1M sodium cyanoborohydride, pH 7.0, through the resin for approximately 6±2 hours at 2°–8° C. The resin was then extensively washed and equilibrated (>40 liters) with 20 mM Tris buffer, 150 mM sodium chloride, pH 7.5, to remove all traces of sodium cyanoborohydride. After the final wash and equilibration, the column effluent showed no detectable levels of sodium cyanoborohydride. The binding capacity of the resin for Factor X was determined to be at least 100 μg/ml.

EXAMPLE 6

Large-scale Production of Highly Purified EGR-Factor Xa: Immunoaffinity Chromatography Purification A Factor X-containing, solvent-detergent treated, partially-purified plasma fraction was obtained from a licensed plasma product manufacturer (Alpha Therapeutic Corporation, City of Industry, Calif.). This material was supplied pre-concentrated and frozen in a sodium citrate/sodium chloride buffer system, pH 6.8. The total protein concentration was measured at between 1.4 and 1.5 mg/ml using a Bradford dye-binding total protein assay (BioRad, Hercules, Calif.). The Factor X concentration was measured at approximately 1.0±0.1 mg/ml based on the results of a reversed-phase HPLC (RP-HPLC) assay and a Factor X deficient coagulation assay (1 Unit=10 μg Factor X), 1.3 liters of the Factor X-containing plasma fraction was thawed for 16–24 hours at 2°–8° C. and then filtered through a 0.2 μm filter (Millipak™ 20, Millipore, Bedford, Mass.) to remove any particulate matter. Based on the resin binding capacity, four cycles of the immunoaffinity column were required to process the 1.3 liters of Factor X-containing plasma fraction. Thus, the filtered Factor X-containing plasma fraction was divided into four roughly equal volumes (330 ml±20 ml) for application to the anti-Factor X immunoaffinity column (prepared as detailed above). For each cycle, the immunoaffinity column (at 2°–8° C.) was equilibrated with 3–5 column volumes of 20 mM Tris buffer, 150 mM sodium chloride, pH 7.5. After equilibration, the filtered Factor X-containing plasma fraction was then loaded at a residence time of less than 5 minutes per column volume and the flow through peak washed to baseline with at least 7 additional column volumes of 20 mM Tris buffer, 150 mM sodium chloride, pH 7.5. The Factor X was eluted with a pH step using 0.1M CAPS buffer, 25 mM sodium chloride pH 10.5. Each immunoaffinity elution pool (in approximately 2–4 column volumes) was immediately titrated to pH 7.5±0.2 with 2.0M HEPES added to 110±10 mM. Absorbance measurements and RP-HPLC confirmed that a total of 1.03±0.03 grams of highly purified Factor X was recovered from the four cycles (236.5 mg, 249.4 mg, 291 mg and 250.5 mg for cycles one through four respectively). Thus, the cumulative yield of Factor X in the elution pools for the immunoaffinity step was 78.0±5.0% and the total Factor X recovery, including Factor X which flowed through the column and was not captured, was 88.0±5.0%. The four elution pools were then stored at 2°–8° C. for one or two days prior to further processing.

EXAMPLE 7

Large-scale Production of Highly Purified EGR-Factor Xa: Filtration and Concentration of Immunoaffinity Elution Pool Because the pools were stored at 2°–8° C., and to add another viral reduction step, the pH-neutralized immunoaffinity elution pools made as described in Example 6 were filtered through a 0.04 μm filter (Sealkleen™ 0.5 ft², Pall Corporation, East Hills, N.Y.) at 2°–8° C. The filtered immunoaffinity elution pools were then concentrated, at 2°–8° C., to 1.0±0.1 mg/ml using a Minisette™ Ultrafiltration system (Filtron, Northborough, Mass.) holding four 0.75 ft² 8 kDa Omega-type ultrafiltration cassettes. The transmembrane pressure was maintained at 15±1 psig, while the cross flow rate and filtrate rates were 2.56±0.2 liters/minutes and 0.28±0.02 liters/minute throughout the course of the concentration step. The final concentration of Factor X was verified by an absorbance measurement at 280 nm. No protein was detected in any of the filtrate samples tested, and the recovery of Factor X for these two steps was thus greater than 99.0%.

EXAMPLE 8

Large-scale Production of Highly Purified EGR-Factor Xa: Activation/inactivation of Factor X The concentrated Factor X made as described in Example 7 was simultaneously activated with Russell's Viper Venom Factor X activating enzyme (RVV-X, Haematologic Technologies, Inc., Essex Junction, Vt.) by the addition of RVV-X to a mass ratio of 250:1 (Factor X:RVV-X), and inactivated with Glu-Gly-Arg-chloromethyl ketone (EGR-ck, Peptisyntha, Brussels, Belgium) added to a molar ratio of 20:1 (EGR-ck:Factor X). The activation reaction was initiated by the addition of 1.0M calcium chloride to a final concentration of 5 mM and performed at ambient room temperature 21°±3° C. The activation reaction was stopped after one hour by the addition of 0.5M EDTA, pH 8.0 to a final concentration of 10 mM. The percent mass conversion of Factor X was greater than 95.0%, as determined by Size-Exclusion-HPLC (SE-HPLC). The final concentrations of Factor X and EGR-Xa after the reaction by RP-HPLC were 0.07 mg/ml and 0.9 mg/ml, respectively. The total mass of EGR-Xa recovered after the reaction step was approximately 882.0±45.0 mg. The post-reaction mixture was held at 2°–8° C. overnight for further processing the next day.

EXAMPLE 9

Large-scale Production of Highly Purified EGR-Factor Xa: Viral Reduction Step In order to clear impurities and contaminants (e.g., virus, RVV-X, and IgG) the reaction mixture made as described in Example 8 was ultrafiltered through a 1 ft$^2$ 70 kDa nominal molecular weight cut-off ultrafiltration module (Viresolve™, Millipore, Bedford, Mass.). Prior to ultrafiltration, the post-reaction mixture was filtered through a 0.45 μm microfilter (Corning, Corning, N.Y.). The filtered post-reaction mixture was then ultrafiltered at a starting cross flow rate of 0.76±0.1 liters/minutes and eventually increased to a final cross flow rate of approximately 1.2±0.1 liters/minutes. The permeate flow rate initially was controlled at 16.0±1.0 ml/minute and then lowered to 8.0±1.0 ml/minute in an attempt to increase recovery. The permeate was continuously tested for protein passage using absorbance measurements and showed a relatively constant 50% passage over the course of the two hour filtration. After the total retained volume reached approximately one hold-up volume or 50±20 ml, the retentate was washed with 50±20 ml using 0.1M CAPS, 25 mM sodium chloride, 110 mM HEPES, pH 7.5. the washing was repeated six more times for a total of seven washes using a total of 425 mls of wash buffer. The EGR-Xa recovery of this step was greater than 90% and the total protein mass balance was 100.0±5.0%.

EXAMPLE 10

Large-scale Production of Highly Purified EGR-Factor Xa: Anion-exchange Chromatography In a final polishing step to minimize contaminants and impurities, the ultrafiltered reaction mixture of Example 9 was then directly loaded onto a 5×20 cm XK chromatography column (Pharmacia, Piscataway, N.J.) containing 125±10 ml DEAE Fractogel™ 650M anion-exchange resin (E. M. Science, Gibbstown, N.J.). The column was pre-equilibrated with 5-10 column volumes of 20 mM Potassium phosphate buffer, 0.2M sodium chloride, 10 mM EDTA, pH 6.5. After completion of the sample load, the column was first washed with 20 mM Potassium phosphate buffer, 10 mM EDTA, pH 6.5, until the flow-through peak had returned to within 10% of baseline. The column was then further washed with 20 mM Potassium phosphate buffer, 0.2M sodium chloride, 10 mM EDTA, pH 6.5, for 5-10 column volumes. The EGR-Xa was then eluted using 20 mM Potassium phosphate buffer, 0.3M sodium chloride, 10 mM EDTA, pH 6.5. The elution peak was collected in 8±1 column volumes. The elution pool was assayed for total protein concentration (Bradford and absorbance measurements), purity (RP-HPLC), residual Factor X and Xa (RP-HPLC and chromogenic, respectively), and residual RVV-X and Anti-Factor X IgG (ELISA). Approximately 750±50 mg of total protein was recovered, containing greater than 95% EGR-Xa (a and β forms in a 30 to 1 ratio), less than 4% Factor X and less than 150 parts per million residual Factor Xa, less than 10 parts per million RVV-X and undetectable levels of Anti-Factor X IgG.

Table 1 summarizes the individual Factor X/EGR-Xa step yields and overall process yield for the production of EGR-Xa from a partially purified Factor X-containing plasma fraction, as described in Examples 10–15. The resulting EGR-Xa product showed greater than 100% clot inhibiting activity in an in vitro clotting assay (aPTT) when compared to a commercially available EGR-Xa standard (Haematologic Technologies, Inc., Essex Junction, Vt.).

TABLE 1

| Factor X Process Yield Summary | |
|---|---|
| Process steps | Yield |
| Immunoaffinity capture efficiency (overall Factor X mass balance approximately 75–85%) | 80.0 ± 10.0% |
| Immunoaffinity step yield | 78.0 ± 5.0% |
| Filtration/Concentration step yield | 99.0 ± 5.0% |
| Reaction step yield | 89.5 ± 5.0% |
| Viral filtration step yield | 90.7 ± 5.0% |
| Anion-exchange step yield | 93.8 ± 5.0% |
| Overall process yield | 58.0 ± 10.0% |

---

I claim:

1. A process for preparing an inhibited form of an activated blood factor, comprising the steps of providing a partially purified preparation containing the blood factor, treating the partially purified preparation to convert the blood factor to an activated blood factor and to convert the activated blood factor to an inhibited form in a single step, and then recovering the resulting inhibited activated blood factor.

2. The process of claim 1 wherein said step of treating the partially purified preparation comprises reacting the preparation with a blood factor activating agent and reacting the preparation with an activated blood factor inhibiting agent.

3. The process of claim 2 wherein said reacting the preparation with a blood factor activating agent and said reacting the preparation with an activated blood factor inhibiting agent are carried out concurrently.

4. The process of claim 2 wherein said reacting the preparation with an activated blood factor inhibiting agent is carried out before said reacting the preparation with a blood factor activating agent is carried out.

5. The process of claim 2 wherein said reacting the preparation with an activated blood factor inhibiting agent is carried out after said reacting the preparation with a blood factor activating agent is carried out.

6. The process of claim 1 wherein said blood factor is Factor X.

7. A process for producing a highly purified preparation of an inhibited form of an activated blood factor, comprising the steps of providing a partially purified preparation containing the blood factor, treating the partially purified preparation to convert the blood factor to an activated blood factor and to convert the activated blood factor to an inhibited form in a single reaction vessel, and then recovering the resulting inhibited activated blood factor.

8. The process of claim 7, wherein said conversion to an activated blood factor and said conversion to an inhibited form are carried out without intervening process steps.

9. The process of claim 7, wherein said inhibited activated blood factor is recovered at the level of purity suitable for pharmaceutical administration.

10. The process of claim 7, wherein the inhibited activated blood factor is recovered using immunoaffinity chromatography utilizing an antigen-specific monoclonal antibody coupled to an activated resin selected from the group consisting of: agarose, cross-linked agarose, dextran, cross-linked polysaccharide, polymethyl methacrylate, and synthetic polymeric-based resin.

11. The process of claim 7, wherein the inhibited activated blood factor is recovered using immunoaffinity chromatography utilizing an antigen-specific monoclonal antibody coupled to an activated resin, and wherein the activated resin utilizes an activation chemistry selected from the group consisting of: tresyl, azlactone, aldehyde, hydrazide, N-hydroxy succinimide and triazine.

12. The process of claim 7, wherein the inhibited activated blood factor is recovered using an anion exchange column having an anion exchange group linked to a naturally derived polysaccharide or a synthetically derived polymeric matrix.

13. The process of claim 7, wherein said partially purified blood factor is treated with an activating enzyme in solution.

14. The process of claim 7, wherein said partially purified blood factor is treated with an immobilized activating enzyme.

15. A process for producing a highly purified preparation of an inhibited form of activated Factor X, comprising steps of providing a partially purified preparation containing Factor X, treating the partially purified preparation concurrently with a Factor X activator and with an activated Factor X inhibitor, and then recovering the resulting inhibited activated Factor X.

16. The process of claim 15 wherein the Factor X activator is selected from the group consisting of Russell's viper venom-X (RVV-X), trypsin, Factor VIIa and Factor IXa.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 306 amino acids
        ( B ) TYPE: amino acid
        ( C ) STRANDEDNESS: single
        ( D ) TOPOLOGY: linear ( i x ) FEATURE:
        ( A ) NAME/KEY: Disulfide-bond
        ( B ) LOCATION: 59..64

( i x ) FEATURE:
        ( A ) NAME/KEY: Disulfide-bond
        ( B ) LOCATION: 79..95

( i x ) FEATURE:
        ( A ) NAME/KEY: Disulfide-bond
        ( B ) LOCATION: 160
        ( D ) OTHER INFORMATION: /note= "Disulfide linkage to residue 132 of SEQ ID NO:2"

(ix) FEATURE:
(A) NAME/KEY: Disulfide-bond
(B) LOCATION: 208..222

(ix) FEATURE:
(A) NAME/KEY: Disulfide-bond
(B) LOCATION: 233..261

(xi) SEQUENCE DESCRIPTION: SEQ ID NO:1:

| Ser | Val | Ala | Gln | Ala | Thr | Ser | Ser | Ser | Gly | Glu | Ala | Pro | Asp | Ser | Ile |
|---|---|---|---|---|---|---|---|---|---|---|---|---|---|---|---|
| 1 | | | | 5 | | | | | 10 | | | | | 15 | |
| Thr | Trp | Lys | Pro | Tyr | Asp | Ala | Ala | Leu | Asp | Pro | Thr | Glu | Asn | Pro | |
| | | | 20 | | | | 25 | | | | | 30 | | | |
| Phe | Asp | Leu | Leu | Asp | Phe | Asn | Gln | Thr | Gln | Pro | Glu | Arg | Gly | Asp | Asn |
| | | 35 | | | | | 40 | | | | | 45 | | | |
| Asn | Leu | Thr | Arg | Ile | Val | Gly | Gly | Gln | Glu | Cys | Lys | Asp | Gly | Glu | Cys |
| | 50 | | | | | 55 | | | | | 60 | | | | |
| Pro | Trp | Gln | Ala | Leu | Leu | Ile | Asn | Glu | Glu | Asn | Glu | Gly | Phe | Cys | Gly |
| 65 | | | | | 70 | | | | | 75 | | | | | 80 |
| Gly | Thr | Ile | Leu | Ser | Glu | Phe | Tyr | Ile | Leu | Thr | Ala | Ala | His | Cys | Leu |
| | | | | 85 | | | | | 90 | | | | | 95 | |
| Tyr | Gln | Ala | Lys | Arg | Phe | Lys | Val | Arg | Val | Gly | Asp | Arg | Asn | Thr | Glu |
| | | | 100 | | | | | 105 | | | | | 110 | | |
| Gln | Glu | Glu | Gly | Gly | Glu | Ala | Val | His | Glu | Val | Glu | Val | Val | Ile | Lys |
| | | 115 | | | | | 120 | | | | | 125 | | | |
| His | Asn | Arg | Phe | Thr | Lys | Glu | Thr | Tyr | Asp | Phe | Asp | Ile | Ala | Val | Leu |
| | 130 | | | | | 135 | | | | | 140 | | | | |
| Arg | Leu | Lys | Thr | Pro | Ile | Thr | Phe | Arg | Met | Asn | Val | Ala | Pro | Ala | Cys |
| 145 | | | | | 150 | | | | | 155 | | | | | 160 |
| Leu | Pro | Glu | Arg | Asp | Trp | Ala | Glu | Ser | Thr | Leu | Met | Thr | Gln | Lys | Thr |
| | | | | 165 | | | | | 170 | | | | | 175 | |
| Gly | Ile | Val | Ser | Gly | Phe | Gly | Arg | Thr | His | Glu | Lys | Gly | Arg | Gln | Ser |
| | | | 180 | | | | | 185 | | | | | 190 | | |
| Thr | Arg | Leu | Lys | Met | Leu | Glu | Val | Pro | Tyr | Val | Asp | Arg | Asn | Ser | Cys |
| | | 195 | | | | | 200 | | | | | 205 | | | |
| Lys | Leu | Ser | Ser | Ser | Phe | Ile | Ile | Thr | Gln | Asn | Met | Phe | Cys | Ala | Gly |
| | 210 | | | | | 215 | | | | | 220 | | | | |
| Tyr | Asp | Thr | Lys | Gln | Glu | Asp | Ala | Cys | Gln | Gly | Asp | Ser | Gly | Gly | Pro |
| 225 | | | | | 230 | | | | | 235 | | | | | 240 |
| His | Val | Thr | Arg | Phe | Lys | Asp | Thr | Tyr | Phe | Val | Thr | Gly | Ile | Val | Ser |
| | | | | 245 | | | | | 250 | | | | | 255 | |
| Trp | Gly | Glu | Gly | Cys | Ala | Arg | Lys | Gly | Lys | Tyr | Gly | Ile | Tyr | Thr | Lys |
| | | | 260 | | | | | 265 | | | | | 270 | | |
| Val | Thr | Ala | Phe | Leu | Lys | Trp | Ile | Asp | Arg | Ser | Met | Lys | Thr | Arg | Gly |
| | | 275 | | | | | 280 | | | | | 285 | | | |
| Leu | Pro | Lys | Ala | Lys | Ser | His | Ala | Pro | Glu | Val | Ile | Thr | Ser | Ser | Pro |
| | 290 | | | | | 295 | | | | | 300 | | | | |
| Leu | Lys | | | | | | | | | | | | | | |
| 305 | | | | | | | | | | | | | | | |

(2) INFORMATION FOR SEQ ID NO:2:

(i) SEQUENCE CHARACTERISTICS:
(A) LENGTH: 139 amino acids
(B) TYPE: amino acid
(C) STRANDEDNESS: single
(D) TOPOLOGY: linear (ix) FEATURE:
  (A) NAME/KEY: Disulfide-bond
  (B) LOCATION: 17..22

(ix) FEATURE:
  (A) NAME/KEY: Disulfide-bond
  (B) LOCATION: 50..61

(ix) FEATURE:
  (A) NAME/KEY: Disulfide-bond
  (B) LOCATION: 55..70

(ix) FEATURE:
  (A) NAME/KEY: Disulfide-bond
  (B) LOCATION: 72..81

(ix) FEATURE:
  (A) NAME/KEY: Disulfide-bond
  (B) LOCATION: 89..100

(ix) FEATURE:
  (A) NAME/KEY: Disulfide-bond
  (B) LOCATION: 96..109

(ix) FEATURE:
  (A) NAME/KEY: Disulfide-bond
  (B) LOCATION: 111..124

(ix) FEATURE:
  (A) NAME/KEY: Disulfide-bond
  (B) LOCATION: 132
  (D) OTHER INFORMATION: /note= "Disulfide linkage with
    residue 160 of SEQ ID NO:1, residue 108 of SEQ ID NO:3 or
    residue 108 of SEQ ID:4"

(xi) SEQUENCE DESCRIPTION: SEQ ID NO:2:

```
Ala Asn Ser Phe Leu Thr Thr Met Lys Lys Gly His Leu Thr Arg Thr
 1               5                  10                 15

Cys Met Thr Thr Thr Cys Ser Tyr Thr Thr Ala Arg Thr Val Phe Thr
             20                  25                  30

Asp Ser Asp Lys Thr Asn Thr Phe Trp Asn Lys Tyr Lys Asp Gly Asp
         35                  40                  45

Gln Cys Glu Thr Ser Pro Cys Gln Asn Gln Gly Lys Cys Lys Asx Gly
     50                  55                  60

Leu Gly Glu Tyr Thr Cys Thr Cys Leu Glu Gly Phe Glu Gly Lys Asn
 65                  70                  75                  80

Cys Glu Leu Phe Thr Arg Lys Leu Cys Ser Leu Asp Asn Gly Asp Cys
                 85                  90                  95

Asp Gln Phe Cys His Glu Glu Gln Asn Ser Val Val Cys Ser Cys Ala
             100                 105                 110

Arg Gly Tyr Thr Leu Ala Asp Asn Gly Lys Ala Cys Ile Pro Thr Gly
         115                 120                 125

Pro Tyr Pro Cys Gly Lys Gln Thr Leu Glu Arg
     130                 135
```

(2) INFORMATION FOR SEQ ID NO:3:

(i) SEQUENCE CHARACTERISTICS:
    (A) LENGTH: 254 amino acids
    (B) TYPE: amino acid
    (C) STRANDEDNESS: single
    (D) TOPOLOGY: linear (ix) FEATURE:
    (A) NAME/KEY: Disulfide-bond
    (B) LOCATION: 7..12

(ix) FEATURE:
    (A) NAME/KEY: Disulfide-bond (B) LOCATION: 27..43

(ix) FEATURE:
(A) NAME/KEY: Disulfide-bond
(B) LOCATION: 108
(D) OTHER INFORMATION: /note= "Disulfide linkage with residue 132 of SEQ ID NO:2"

(ix) FEATURE:
(A) NAME/KEY: Disulfide-bond
(B) LOCATION: 156..170

(ix) FEATURE:
(A) NAME/KEY: Disulfide-bond
(B) LOCATION: 181..209

(xi) SEQUENCE DESCRIPTION: SEQ ID NO:3:

```
Ile Val Gly Gly Gln Glu Cys Lys Asp Gly Glu Cys Pro Trp Gln Ala
1               5                   10                  15
Leu Leu Ile Asn Glu Glu Asn Glu Gly Phe Cys Gly Gly Thr Ile Leu
                20                  25                  30
Ser Glu Phe Tyr Ile Leu Thr Ala Ala His Cys Leu Tyr Gln Ala Lys
            35              40                  45
Arg Phe Lys Val Arg Val Gly Asp Arg Asn Thr Glu Gln Glu Glu Gly
        50                  55                  60
Gly Glu Ala Val His Glu Val Glu Val Val Ile Lys His Asn Arg Phe
65                  70                  75                  80
Thr Lys Glu Thr Tyr Asp Phe Asp Ile Ala Val Leu Arg Leu Lys Thr
                85                  90                  95
Pro Ile Thr Phe Arg Met Asn Val Ala Pro Ala Cys Leu Pro Glu Arg
            100                 105                 110
Asp Trp Ala Glu Ser Thr Leu Met Thr Gln Lys Thr Gly Ile Val Ser
        115                 120                 125
Gly Phe Gly Arg Thr His Glu Lys Gly Arg Gln Ser Thr Arg Leu Lys
    130                 135                 140
Met Leu Glu Val Pro Tyr Val Asp Arg Asn Ser Cys Lys Leu Ser Ser
145                 150                 155                 160
Ser Phe Ile Ile Thr Gln Asn Met Phe Cys Ala Gly Tyr Asp Thr Lys
                165                 170                 175
Gln Glu Asp Ala Cys Gln Gly Asp Ser Gly Gly Pro His Val Thr Arg
            180                 185                 190
Phe Lys Asp Thr Tyr Phe Val Thr Gly Ile Val Ser Trp Gly Glu Gly
        195                 200                 205
Cys Ala Arg Lys Gly Lys Tyr Gly Ile Tyr Thr Lys Val Thr Ala Phe
210                 215                 220
Leu Lys Trp Ile Asp Arg Ser Met Lys Thr Arg Gly Leu Pro Lys Ala
225                 230                 235                 240
Lys Ser His Ala Pro Glu Val Ile Thr Ser Ser Pro Leu Lys
                245                 250
```

(2) INFORMATION FOR SEQ ID NO:4:

(i) SEQUENCE CHARACTERISTICS:
(A) LENGTH: 241 amino acids
(B) TYPE: amino acid
(C) STRANDEDNESS: single
(D) TOPOLOGY: linear (ix) FEATURE:
(A) NAME/KEY: Disulfide-bond
(B) LOCATION: 7..12

(ix) FEATURE:

-continued

```
         ( A ) NAME/KEY: Disulfide-bond
         ( B ) LOCATION: 27..43

( i x ) FEATURE:
         ( A ) NAME/KEY: Disulfide-bond
         ( B ) LOCATION: 108
         ( D ) OTHER INFORMATION: /note= "Disulfide linkage with
               residue 132 of SEQ ID NO:2"

( i x ) FEATURE:
         ( A ) NAME/KEY: Disulfide-bond
         ( B ) LOCATION: 156..170

( i x ) FEATURE:
         ( A ) NAME/KEY: Disulfide-bond
         ( B ) LOCATION: 181..209

( x i ) SEQUENCE DESCRIPTION: SEQ ID NO:4:
```

| Ile | Val | Gly | Gly | Gln | Glu | Cys | Lys | Asp | Gly | Glu | Cys | Pro | Trp | Gln | Ala |
|---|---|---|---|---|---|---|---|---|---|---|---|---|---|---|---|
| 1 | | | | 5 | | | | | 10 | | | | | 15 | |
| Leu | Leu | Ile | Asn | Glu | Glu | Asn | Glu | Gly | Phe | Cys | Gly | Gly | Thr | Ile | Leu |
| | | | 20 | | | | | 25 | | | | | 30 | | |
| Ser | Glu | Phe | Tyr | Ile | Leu | Thr | Ala | Ala | His | Cys | Leu | Tyr | Gln | Ala | Lys |
| | | 35 | | | | | 40 | | | | | 45 | | | |
| Arg | Phe | Lys | Val | Arg | Val | Gly | Asp | Arg | Asn | Thr | Glu | Gln | Glu | Glu | Gly |
| | 50 | | | | | 55 | | | | | 60 | | | | |
| Gly | Glu | Ala | Val | His | Glu | Val | Glu | Val | Val | Ile | Lys | His | Asn | Arg | Phe |
| 65 | | | | | 70 | | | | | 75 | | | | | 80 |
| Thr | Lys | Glu | Thr | Tyr | Asp | Phe | Asp | Ile | Ala | Val | Leu | Arg | Leu | Lys | Thr |
| | | | | 85 | | | | | 90 | | | | | 95 | |
| Pro | Ile | Thr | Phe | Arg | Met | Asn | Val | Ala | Pro | Ala | Cys | Leu | Pro | Glu | Arg |
| | | | 100 | | | | | 105 | | | | | 110 | | |
| Asp | Trp | Ala | Glu | Ser | Thr | Leu | Met | Thr | Gln | Lys | Thr | Gly | Ile | Val | Ser |
| | | 115 | | | | | 120 | | | | | 125 | | | |
| Gly | Phe | Gly | Arg | Thr | His | Glu | Lys | Gly | Arg | Gln | Ser | Thr | Arg | Leu | Lys |
| | 130 | | | | | 135 | | | | | 140 | | | | |
| Met | Leu | Glu | Val | Pro | Tyr | Val | Asp | Arg | Asn | Ser | Cys | Lys | Leu | Ser | Ser |
| 145 | | | | | 150 | | | | | 155 | | | | | 160 |
| Ser | Phe | Ile | Ile | Thr | Gln | Asn | Met | Phe | Cys | Ala | Gly | Tyr | Asp | Thr | Lys |
| | | | | 165 | | | | | 170 | | | | | 175 | |
| Gln | Glu | Asp | Ala | Cys | Gln | Gly | Asp | Ser | Gly | Gly | Pro | His | Val | Thr | Arg |
| | | | 180 | | | | | 185 | | | | | 190 | | |
| Phe | Lys | Asp | Thr | Tyr | Phe | Val | Thr | Gly | Ile | Val | Ser | Trp | Gly | Glu | Gly |
| | | 195 | | | | | 200 | | | | | 205 | | | |
| Cys | Ala | Arg | Lys | Gly | Lys | Tyr | Gly | Ile | Tyr | Thr | Lys | Val | Thr | Ala | Phe |
| | 210 | | | | | 215 | | | | | 220 | | | | |
| Leu | Lys | Trp | Ile | Asp | Arg | Ser | Met | Lys | Thr | Arg | Gly | Leu | Pro | Lys | Ala |
| 225 | | | | | 230 | | | | | 235 | | | | | 240 |
| Lys | | | | | | | | | | | | | | | |